United States Patent [19]

Tanaka et al.

[11] 4,418,192
[45] Nov. 29, 1983

[54] ANTHRACYCLINONE TRISACCHARIDE COMPOUNDS

[75] Inventors: Hiroshi Tanaka, Fujisawa; Takeo Yoshioka, Ayase; Yasutaka Shimauchi, Ninomiya; Toshikazu Oki, Yokohama; Tomoyuki Ishikura, Chigasaki; Tomio Takeuchi; Hamao Umezawa, both of Tokyo, all of Japan

[73] Assignee: Sanraku-Ocean Co., Ltd., Tokyo, Japan

[21] Appl. No.: 370,212

[22] Filed: Apr. 20, 1982

[30] Foreign Application Priority Data

Apr. 23, 1981 [JP] Japan .................................. 56-61766

[51] Int. Cl.³ ...................... A61K 31/71; C07H 15/24
[52] U.S. Cl. ...................................... 536/6.4; 424/180
[58] Field of Search ................. 536/6.4, 4.1; 424/180; 204/158 N

[56] References Cited

U.S. PATENT DOCUMENTS

| | | | |
|---|---|---|---|
| 3,772,269 | 11/1973 | Lew | 536/4.1 |
| 4,039,663 | 8/1977 | Arcamone et al. | 536/6.4 |
| 4,169,142 | 9/1979 | Penco et al. | 536/6.4 |
| 4,216,208 | 8/1980 | De Barbieri | 424/180 |
| 4,316,011 | 2/1982 | Oki et al. | 424/180 |
| 4,318,790 | 3/1982 | Wiley | 204/158 N |

FOREIGN PATENT DOCUMENTS

| | | | |
|---|---|---|---|
| 55-104225 | 8/1980 | Japan | 536/6.4 |
| 55-108889 | 8/1980 | Japan | 536/6.4 |

OTHER PUBLICATIONS

Oki et al. *The Journal of Antibiotics*, "New Antitumor Antibiotics A and B," vol. 28, No. 10, Oct. 1975, pp. 830-834.

*Primary Examiner*—Johnnie R. Brown
*Assistant Examiner*—Elli Peseler
*Attorney, Agent, or Firm*—Jordan and Hamburg

[57] ABSTRACT

Disclosed are novel anthracyclinone glycosides represented by the chemical formula

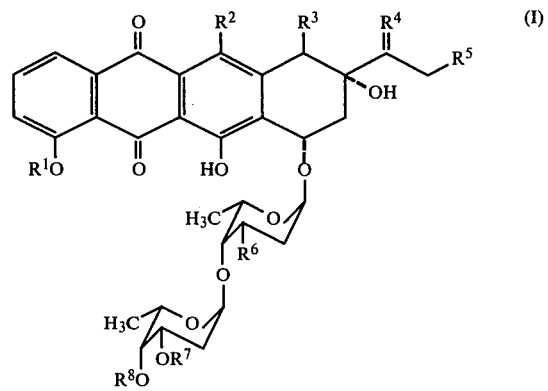

wherein
$R^1$ is hydrogen or methyl;
$R^2$ is hydrogen or hydroxyl;
$R^3$ is hydrogen or methoxycarbonyl;
$R^4$ is two hydrogen atoms or an oxygen atom;
$R^5$ is hydrogen, hydroxyl or —OCOX (wherein X is lower alkyl or aralkyl);
$R^6$ is amino, monomethylamino or dimethylamino;
$R^7$ is hydrogen or acetyl; and
$R^8$ is hydrogen or L-cinerulose A

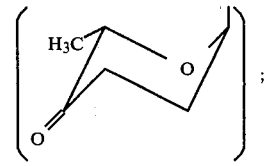

but, when $R^1$ and $R^3$ are hydrogen and methoxycarbonyl respectively, $R^2$ is hydrogen; $R^4$ is two hydrogen atoms; $R^5$ is hydrogen; $R^6$ is amino, monoethylamino or dimethylamino; $R^7$ is acetyl; and $R^8$ is L-cinerulose A, and their acid addition salts and a method for preparation thereof which consists of treating O-alpha-L-cinerulosyl-(1→4)-O-(3-O-acetyl-2-deoxy-alpha-L-fucosyl)-(1→4)-alpha-L-rhodosamine with corresponding aglycones.

7 Claims, No Drawings

ANTHRACYCLINONE TRISACCHARIDE COMPOUNDS

BACKGROUND OF THE INVENTION

(1) Field of the Invention

The present invention relates to novel antitumor anthracyclinone glycosides and their preparation method.

(2) Description of the Prior Art

Various types of anthracyclinone glycosides have been provided by fermentative, semi-synthetic and fully synthetic processes. For example, adriamycin (U.S. Pat. No. 3,803,124), carminomycin (J. Antibiotics 27, 254 (1974)), dihydrocarminomycin (Antibiotiki 21, 1008 (1976)) and rhodomycin analogs (Japan Kokai No. 56-15299 (1981)) have been reported (a review article is found in the Japanese Journal of Antibiotics 30, S-70~S-84 (1977). Among this family of antibiotics, adriamycin and daunomycin (U.S. Pat. No. 3,616,242) which have widely been used clinically as antitumor chemotherapeutics are known to often cause undesirable side effects.

SUMMARY OF THE INVENTION

The present invention relates to novel anthracylinone glycosides represented by the chemical formula

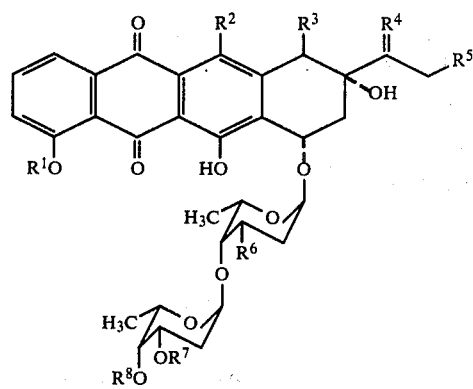

wherein
$R^1$ is hydrogen or methyl;
$R^2$ is hydrogen or hydroxyl;
$R^3$ is hydrogen or methoxycarbonyl;
$R^4$ is two hydrogen atoms or an oxygen atom;
$R^5$ is hydrogen, hydroxyl or —OCOX (wherein X is lower alkyl or aralkyl);
$R^6$ is amino, monomethylamino or dimethylamino;
$R^7$ is hydrogen or acetyl;
$R^8$ is hydrogen or L-cinerulose A

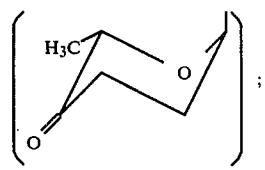

but, when $R^1$ and $R^3$ are hydrogen methoxycarbonyl respectively, $R^2$ is hydrogen; $R^4$ is two hydrogen atoms; $R^5$ is hydrogen; $R^6$ is amino, monomethylamino or dimethylamino; $R^7$ is acetyl; and $R^8$ is L-cinerulose A, and their acid addition salts; and to a method for preparation thereof which consists of treating under suitable glycosidation conditions anthracyclinones represented by the chemical formula

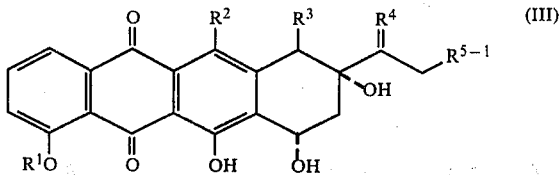

wherein
$R^1$, $R^2$, $R^3$ and $R^4$ have the same meanings as defined above; and
$R^{5-1}$ is hydrogen or —OCOX (wherein X is lower alkyl or aralkyl),
with a sugar compound represented by the chemical formula

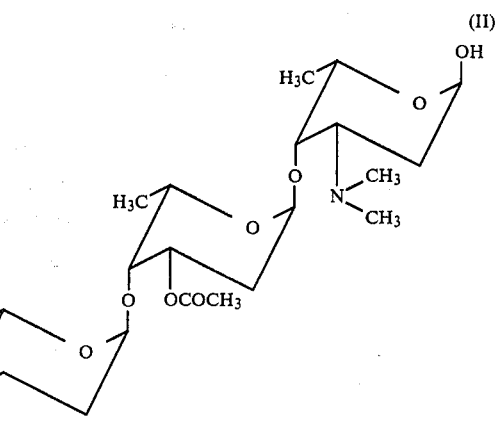

or its reactive derivatives, and, if desired, converting said reaction products to other anthracyclinone glycoside derivatives. The compounds of the present invention have a potent antitumor activity, but are less toxic than daunomycin and adriamycin.

DETAILED DESCRIPTION OF THE INVENTION

The present invention relates to antitumor anthracycline antibiotics. More particularly, it is concerned with novel antitumor anthracyclinone glycosides represented by the chemical formula

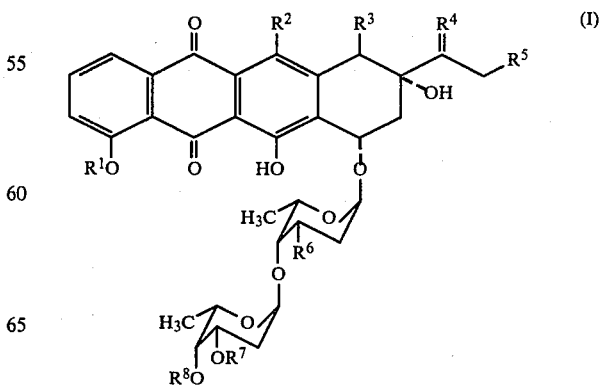

wherein

R$^1$ is hydrogen or methyl;

R$^2$ is hydrogen or hydroxyl;

R$^3$ is hydrogen or methoxycarbonyl;

R$^4$ is two hydrogen atoms or an oxygen atom;

R$^5$ is hydrogen, hydroxyl or —OCOX (wherein X is lower alkyl or aralkyl);

R$^6$ is amino, monomethylamino or dimethylamino;

R$^7$ is hydrogen or acetyl; and

R$^8$ is hydrogen or L-cinerulose A

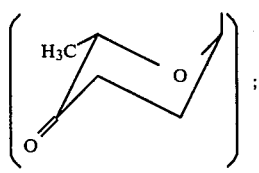

but, when R$^1$ and R$^3$ are hydrogen and methoxycarbonyl respectively, R$^2$ is hydrogen; R$^4$ is two hydrogen atoms; R$^5$ is hydrogen; R$^6$ is amino, monomethylamino or dimethylamino; R$^7$ is acetyl; and R$^8$ is L-cinerulose A, and their acid addition salts, and with a method for preparation of such compounds. Adriamycin and daunomycin are characterized by possessing a daunosaminyl group

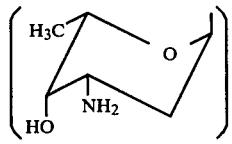

in their glycoside parts.

Aclacinomycin A which has been described as a less cardio-toxic anthracycline by some of the present authors in U.S. Pat. No. 3,988,315 and Jap. P. No. 864,851 structurally differs from adriamycin and daunomycin in its linear trisaccharide (L-rhodosamine, 2-deoxy-L-fucose and L-cinerulose A; these sugars will be abbreviated hereafter to R, D and C respectively).

In an approach to obtain new anthracyclin derivatives having less harmful side effects than daunomycin and adriamycin, we have succeeded in synthesis of novel anthracyclinone glycosides represented by chemical formula (I) by treating a trisaccharide represented by the chemical formula

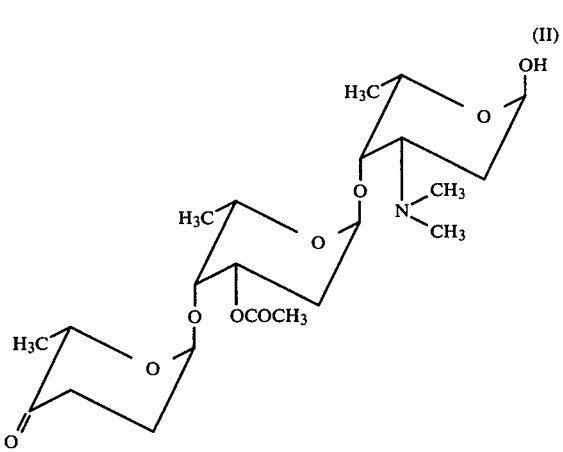

(O-alpha-L-cinerulosyl-(1→4)-O-(3-O-acetyl-2-deoxyalpha-L-fucosyl)-(1→4)-alpha-L-rohodosamine; this sugar which will be abbreviated to 3''-O-acetyl RDC hereafter can be obtained by hydrogenolysis of 4,6,3''-O-triacetylaclacinomycin A) with various anthracyclinone compounds such as alkavinone (abbreviated to AKN hereafter), daunomycinone (abbreviated to DMN hereafter), adriamycinone (abbreviated to AMN hereafter) and carminomycinone (abbreviated to CMN hereafter) to form the glycoside bond at the 7-position of the aglycone, and if necessary, hydrolyzing said reaction products.

The anthracyclinone glycosides of the present invention are novel and hitherto unknown in the literature, as they differ from daunomycin, adriamycin and carminomycin derivatives in the sugar moiety derived from 3'-O-acetyl RDC instead of the L-daunosaminyl moiety, and from aclacinomycin A in 3'-O-acetyl RDC instead of RDC. The compounds of the present invention represented by chemical formula (I) show marked antitumor effects in examination with experimental animal tumors and in vitro tests, but are far less toxic than daunomycin and adriamycin.

In the present specification, the lower alkyl contains 1–5 carbon atoms and may be straight or branched, while the aralkyl is preferably phenyl-lower alkyl. Table 1 elucidates some typical examples of the anthracyclinone glycosides represented by chemical formula (I) according to the present invention.

TABLE 1

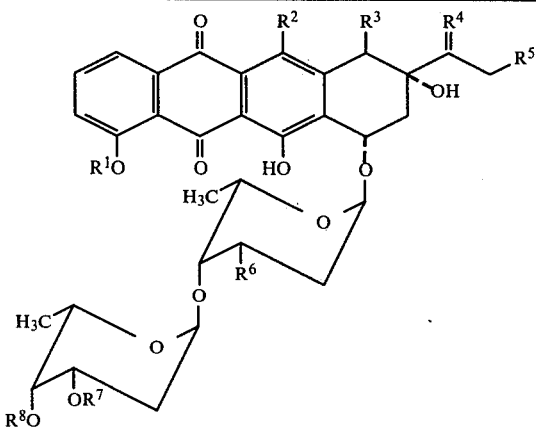

| Compounds | $R^1$ | $R^2$ | $R^3$ | $R^4$ | $R^5$ | $R^6$ | $R^7$ | $R^8$ |
|---|---|---|---|---|---|---|---|---|
| 3″-O—acetyl AKN—RDC | H | H | $CO_2CH_3$ | $H_2$ | H | $N(CH_3)_2$ | $COCH_3$ | L-cinerulose A |
| 3″-O—acetyl AKN—DmDC | H | H | $CO_2CH_3$ | $H_2$ | H | $NHCH_3$ | $COCH_3$ | L-cinerulose A |
| 3″-O—acetyl AKN—DaDC | H | H | $CO_2CH_3$ | $H_2$ | H | $NH_2$ | $COCH_3$ | L-cinerulose A |
| 3″-O—acetyl DMN—RDC | $CH_3$ | OH | H | O | H | $N(CH_3)_2$ | $COCH_3$ | L-cinerulose A |
| 3″-O—acetyl DMN—DmDC | $CH_3$ | OH | H | O | H | $NHCH_3$ | $COCH_3$ | L-cinerulose A |
| 3″-O—acetyl DMN—DaDC | $CH_3$ | OH | H | O | H | $NH_2$ | $COCH_3$ | L-cinerulose A |
| DMN—RDC | $CH_3$ | OH | H | O | H | $N(CH_3)_2$ | H | L-cinerulose A |
| DMN—DmDC | $CH_3$ | OH | H | O | H | $NHCH_3$ | H | L-cinerulose A |
| DMN—DaDC | $CH_3$ | OH | H | O | H | $NH_2$ | H | L-cinerulose A |
| DMN—RD | $CH_3$ | OH | H | O | H | $N(CH_3)_2$ | H | H |
| DMN—DmD | $CH_3$ | OH | H | O | H | $NHCH_3$ | H | H |
| DMN—DaD | $CH_3$ | OH | H | O | H | $NH_2$ | H | H |
| 14,3″-O—di-acetyl AMN—RDC | $CH_3$ | OH | H | O | $OCOCH_3$ | $N(CH_3)_2$ | $COCH_3$ | L-cinerulose A |
| 14,3″-O—di-acetyl AMN—DmDC | $CH_3$ | OH | H | O | $OCOCH_3$ | $NHCH_3$ | $COCH_3$ | L-cinerulose A |
| 14,3″-O—di-acetyl AMN—DaDC | $CH_3$ | OH | H | O | $OCOCH_3$ | $NH_2$ | $COCH_3$ | L-cinerulose A |
| 14-O—phenyl-acetyl-3″-O—acetyl AMN—RDC | $CH_3$ | OH | H | O | $OCOCH_2{-}C_6H_5$ | $N(CH_3)_2$ | $COCH_3$ | L-cinerulose A |
| 14-O—phenyl-acetyl-3″-O—acetyl AMN—DmDC | $CH_3$ | OH | H | O | $OCOCH_2{-}C_6H_5$ | $NHCH_3$ | $COCH_3$ | L-cinerulose A |
| 14-O—phenyl-acetyl-3″-O—acetyl AMN—DaDC | $CH_3$ | OH | H | O | $OCOCH_2{-}C_6H_5$ | $NH_2$ | $COCH_3$ | L-cinerulose A |
| 3″-O—acetyl AMN—RDC | $CH_3$ | OH | H | O | OH | $N(CH_3)_2$ | $COCH_3$ | L-cinerulose A |
| 3″-O—acetyl AMN—DmDC | $CH_3$ | OH | H | O | OH | $NHCH_3$ | $COCH_3$ | L-cinerulose A |
| 3″-O—acetyl AMN—DaDC | $CH_3$ | OH | H | O | OH | $NH_2$ | $COCH_3$ | L-cinerulose A |
| AMN—RDC | $CH_3$ | OH | H | O | OH | $N(CH_3)_2$ | H | L-cinerulose A |
| AMN—DmDC | $CH_3$ | OH | H | O | OH | $NHCH_3$ | H | L-cinerulose A |
| AMN—DaDC | $CH_3$ | OH | H | O | OH | $NH_2$ | H | L-cinerulose A |
| AMN—RD | $CH_3$ | OH | H | O | OH | $N(CH_3)_2$ | H | H |
| AMN—DmD | $CH_3$ | OH | H | O | OH | $NHCH_3$ | H | H |
| AMN—DaD | $CH_3$ | OH | H | O | OH | $NH_2$ | H | H |
| 3″-O—acetyl CMN—RDC | H | OH | H | O | H | $N(CH_3)_2$ | $COCH_3$ | L-cinerulose A |
| 3″-O—acetyl | H | OH | H | O | H | $NHCH_3$ | $COCH_3$ | L-cinerulose A |

TABLE 1-continued

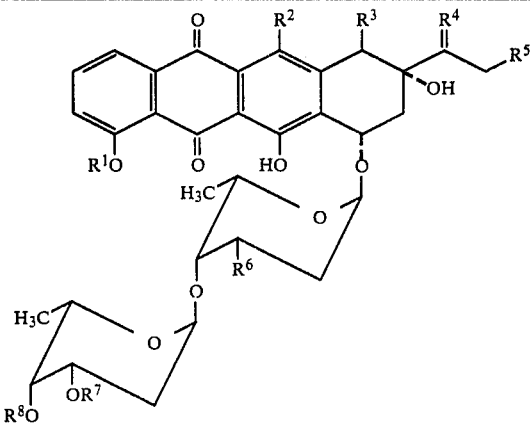

| Compounds | $R^1$ | $R^2$ | $R^3$ | $R^4$ | $R^5$ | $R^6$ | $R^7$ | $R^8$ |
|---|---|---|---|---|---|---|---|---|
| CMN—DmDC 3″-O—acetyl | H | OH | H | O | H | $NH_2$ | $COCH_3$ | L-cinerulose A |
| CMN—DaDC | | | | | | | | |
| CMN—RDC | H | OH | H | O | H | $N(CH_3)_2$ | H | L-cinerulose A |
| CMN—DmDC | H | OH | H | O | H | $NHCH_3$ | H | L-cinerulose A |
| CMN—DaDC | H | OH | H | O | H | $NH_2$ | H | L-cinerulose A |
| CMN—RD | H | OH | H | O | H | $N(CH_3)_2$ | H | H |
| CMN—DmD | H | OH | H | O | H | $NHCH_3$ | H | H |
| CMN—DaD | H | OH | H | O | H | $NH_2$ | H | H |

AKN: aklavinone
DMN: daunomycinone
AMN: adriamycinone
CMN: carminomycinone
R: L-rhodosamine
D: 2-deoxy-L-fucose
C: L-cinerulose A
Dm: N—monomethyl-L-daunosamine
Da: L-daunosamine Because of basicity, the compounds of the present invention represented by chemical formula (I) can form acid addition salts. It is preferable to make acid addition salts with pharmaceutically permissible acids. For example, inorganic acids such as hydrochloric acid, hydrobromic acid, sulfuric acid and phosphoric acid; and organic acids such as acetic acid, propionic acid, maleic acid, oleic acid, palmitic acid, citric acid, succinic acid, tartaric acid, fumaric acid, glutamic acid, pantothenic acid, laurylsulfonic acid, methanesulfonic acid and naphthalenesulfonic acid are employable in the present invention.

The anthracyclinone glycosides of chemical formula (I) provided by the present invention are produced by treating under suitable glycosidation conditions the sugar compound (trisaccharide represented by chemical formula (II)) or its reactive derivatives with corresponding anthracyclinones (aglycones) or their functional derivatives.

(1) Sugar compound

The sugar compound employed in the present invention is a trisaccharide represented by chemical formula (II) (3′-O-acetyl RDC).

The compound represented by chemical formula (II) can be purposively produced by many methods. One of the preferred methods is explained in the followings:

Aclacinomycin A is quantitatively converted to 4,6,3″-O-triacetylaclacinomycin A by acetylation at room temperature for 10-20 hours in a mixture of acetic anhydride and pyridine. Then 4,6,3″-O-triacetylaclacinomycin A in a suitable organic solvent such as lower alcohols (for example, methanol) is quantitatively hydrogenated in the presence of a hydrogenation catalyst such as palladium/barium sulfate, palladium/carbon and platinum oxide to give the trisaccharide (3′-O-acetyl RDC) represented by chemical formula (II) which is composed of L-rhodosamine, L-2-deoxy-3-O-acetylfucose and L-cinerulose A linked in linear fashion through the alpha-glycoside bondage. When 5% palladium/barium sulfate is used as catalyst, the quantitative ratio of the reaction mixture to the catalyst is preferably about 1/1. Lower alcohols can be favorably employed as solvent. The hydrogenation is usually completed in 0.5-2 hours.

It is advantageous to recover the trisaccharide from the reaction mixture by solvent extraction. More particularly, after solids are removed by filtration, the solution is concentrated to dryness under reduced pressure to yield a yellowish brown oil. This oil is dissolved in a small volume of chloroform and then subjected to extraction with 0.5-5% acetic acid. The aqueous layer is separated and rinsed several times with small volumes of chloroform for complete removal of pigmented matters. The rinsed aqueous solution is made alkaline with sodium bicarbonate and the trisaccharide is extracted several times with chloroform. The chloroform extracts are combined, dried over anhydrous sodium sulfate and concentrated to dryness under reduced pressure to give a high yield of a white powder largely composed of 3′-O-acetyl RDC (chemical formula (II); alpha-anomers at C-1, C-1′ and C-1″)

(2) Aglycone compounds

All anthracyclinone compounds represented by the following formula

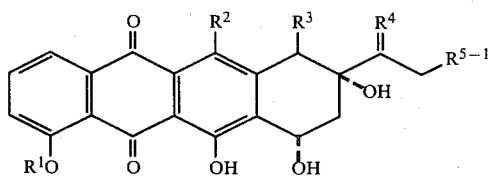

wherein
R¹ is hydrogen or methyl;
R² is hydrogen or hydroxyl;
R³ is hydrogen or methoxycarbonyl;
R⁴ is two hydrogen atoms or an oxygen atom; and
R$^{5-1}$ is hydrogen or —OCOX (wherein X is lower alkyl or aralkyl)

can be employed as aglycone compound in the present invention. These anthracyclinone compounds can be synthesized by modifications of the method of aglycone synthesis described by F, Arcamone in "Topics in Antibiotic Chemistry," Vol. 2, pp. 99–239, Elis Horwood Limited. In addition, the following aglycones and their derivatives can easily be obtained by acid hydrolysis from the corresponding anthracycline antibiotics, that is, aclacinomycin A, daunomycin, adriamycin and carminomycin.

TABLE 2

| Aglycone | Formula (III) | | | | |
|---|---|---|---|---|---|
| | R¹ | R² | R³ | R⁴ | R$^{5-1}$ |
| Aklavinone (AKN) | H | H | COOCH₃ | H₂ | H |
| Daunomycinone (DMN) | CH₃ | OH | H | O | H |
| Adriamycinone (AMN) | CH₃ | OH | H | O | OH |
| Carminomycinone (CMN) | H | OH | H | O | H |

Among these anthracyclinone compounds, AMN has a primary hydroxyl group at position 14 which needs to be protected with suitable groups for selective glycosidation at the 7-hydroxyl group. After extensive studies for selective protection of the 14-hydroxyl group of AMN, the present authors have discovered that AMN in a mixture of boric acid and acetic anhydride is selectively acetylated at position 14 in the presence of pyridine to give 14-O-acetyl AMN (R¹=CH₃, R²=OH, R³=H, R⁴=O and R$^{5-1}$=OCOCH₃ in chemical formula (III)). Furthermore AMN derivatives esterified at position 14 can be prepared from daunomycin by conventional methods. For example, daunomycin hydrochloride is brominated at position 14 and then hydrolyzed to give 14-bromo DMN. Treatment of this anthracyclinone with sodium carboxylates in acetone yields 14-esterified AMN such as 14-O-acetyl AMN and 14-O-phenylacetyl AMN.

Various anthracyclinone derivatives thus obtained are used in the following glycosidation reaction.

(3) Glycosidation

The glycosidation of anthracyclinone compounds by 3'-O-acetyl RDC is described by J. Leroux and A. S. Perlin (Carbohydrate Research 67, 163–178, 1978). This method has an advantage that a sequence of sulfonylation, halogenation and glycosidation can be carried out in one batch, but has never applied to the glycosidation of anthracyclinone with trisaccharides.

The present authors have obtained a 20–40% yield of novel anthracyclinone glycosides containing trisaccharide by glycosidation of various anthracyclinone compounds with 3'-O-acetyl RDC. The outline of this glycosidation reaction is briefly explained below.

3'-O-Acetyl RDC is dissolved in an inert organic solvent such as dichloromethane, chloroform and tetrahydrofuran and then treated with trifluoromethanesulfonic anhydride at a low temperature (for example, −70° C.) or with methanesulfonyl chloride, methanesulfonic anhydride or paratoluenesulfonyl chloride at a temperature in the range of −10°−−20° C., in the presence of 2,6- or 2,4,6-lower alkyl-pyridine such as 2,6-lutidine and 2,4,6-collidine and tetraalkylammonium bromide such as tetra-n-butylammonium bromide. After anthracyclinone is added, the temperature of the reaction mixture is raised to 10°–30° C. and kept there for a period of 2–24 hours until the glycosidation is completed. The extent of glycosidation is monitored by thin layer chromatography using a developing solvent system of chloroform/methanol (10/1). The reaction mixture is diluted with an organic solvent such as benzene, toluene, ethyl acetate and chloroform and then rinsed with 1% sodium bicarbonate, 5% monopotassium phosphate and water. The organic solvent is removed by evaporation under reduced pressure and the residue is subjected to silica gel column chromatography or preparative silica gel thin layer chromatography to provide a pure preparation of a novel anthracyclinone glycoside in which 3'-O-acetyl RDC is linked to the 7-position of aglycone through glycoside bond.

Using the above-described method, the 7-hydroxyl groups of AKN, DMN, 14-O-acetyl (or phenylacetyl) AMN and CMN were allowed to react with 3'-O-acetyl RDC to give 3"-O-acetyl AKN-RDC, 3" -O-acetyl DMN-RDC, 14-O-acetyl (or phenylacetyl)-3"-O-acetyl AMN-RDC and 3"-O-acetyl CMN-RDC, respectively.

(4) Deprotection

Deprotection at position 3" or positions 14 and 3" of the anthracyclinone glycosides obtained in (3) is accomplished by hydrolysis in an aqueous solution of 3–10 equivalents (preferably 5 equivalents) of potassium carbonate, sodium carbonate or sodium hydroxide with or without an organic solvent such as methanol, acetone and tetrahydrofuran. After treatment, the reaction mixture is neutralized with a weak acid such as acetic acid and monopotassium phosphate; and is again made alkaline with sodium bicarbonate and the like. The solution is subjected to extraction with an organic solvent such as chloroform, ethyl acetate and benzene. The organic extract is recovered and concentrated to dryness under reduced pressure to give a crude preparation of deprotected anthracyclinone glycoside. Purification by silica gel chromatography yields pure preparations of anthracyclinone glycosides deprotected at position 3", position 14 and positions 3" and 14.

During this alkaline treatment, the byproduction of anthracyclinone disaccharide containing no terminal L-cinerulose A was observed. For example, on alkaline hydrolysis of 3"-O-acetyl DMN-RDC, DMN-RDC (3"-deacetylated product) and DMN-RD (3"-deacetylated product containing no terminal L-cinerulose A) are produced.

On alkaline hydrolysis of 14-O-acetyl (or phenylacetyl) AMN-RDC, the 14-deacetylation (or de-phenylacetylation) preferentially occurs in an initial phase of reaction to give 3"-O-acetyl AMN-RDC. When the hydrolysis is continued for a further period, AMN-RDC and AMN-RD (product resulting from 3"-O-acetyl AMN-RDC by 3"-deacetylation and removal of terminal L-cinerulose A) are obtained. Similarly CMN-RDC and CMN-RD can be prepared from 3"-O-acetyl CMN-RDC.

(5) Demethylation

Anthracyclinone glycosides obtained by the method of the present invention can be de-N-methylated by light irradiation. For instance, when DMN-RDC in (4) is dissolved in an organic solvent such as chloroform, benzene, acetone and methanol and then irradiated under the sun light for a period of several hours, two anthracyclinone glycoside products are produced in which the 3'-dimethylamino group of DMN-RDC is demethylated to the 3'-monomethylamino and further to the 3'-amino group. The de-N-methylation by light irradiation is also applicable to other anthracyclinone glycosides.

The anthracyclinone glycoside compounds represented by chemical formula (I) of the present invention can be converted to their acid addition salts with above-defined inorganic or organic acids by suitable methods known per se.

The antitumor activities of the anthracyclinone glycosides represented by chemical formula (I) of the present invention can experimentally be demonstrated as described in the followings:

(1) Antitumor activity

After intraperitoneal transplantation of L 1210 leukemia cells ($1 \times 10^5$ cells/mouse), 0.25 ml/animal of solutions of one of the anthracyclinone glycosides (HCl salts) of the present invention in physiological saline was intraperitoneally injected to $CDF_1$ mice every day for 9 days. The mice were observed for 30 days. Table 3 shows the antitumor effects of the anthracyclinone glycosides of the present invention expressed in the prolongation rate of the survival time as 100 in the control mice receiving physiological saline only.

TABLE 2

| Compounds | Prolongation rate of the survival time (T/C) (%) Dose (mg/kg/day) | | | | | | |
|---|---|---|---|---|---|---|---|
| | 10 | 7.5 | 5 | 2.5 | 1.25 | 0.63 | 0.32 |
| 3''-O—acetyl AKN—RDC | 180 | 186 | 168 | 114 | — | — | — |
| 3''-O—acetyl DMN—RDC | — | 164 | 210 | 180 | 144 | 114 | — |
| DMN—RDC | — | — | 126 | 187 | 184 | 135 | 126 |
| DMN—RD | — | — | 120 | 165 | 172 | 144 | 114 |
| 3''-O—acetyl AMN—RDC | — | — | — | 96 | 140 | 165 | 144 |
| AMN—RDC | — | — | 130 | 145 | 158 | 142 | 114 |
| 3''-O—acetyl CMN—RDC | 165 | 214 | 208 | 159 | 124 | — | — |
| CMN—RDC | — | 145 | 180 | 160 | 132 | — | — |

T: group of treated mice
C: group of control mice receiving physiological saline only.

(2) Biochemical Properties

The anthracyclinone glycosides compounds of the present invention markedly inhibited the growth of mouse leukemia cells (L 1210) as well as the nucleic acid synthesis in the cells.

L 1210 culture cells ($5 \times 10^4$ cells/ml; final cell concentration) were inoculated to RPMI 1640 medium (Roswell Park Memorial Institute 1640 medium) containing 20% calf serum and then one of the anthracyclinone glycosides listed in Table 4 was added to make a final concentration of 0.1–5 µg/ml. After incubation at 37° C. for 2 days in a $CO_2$ incubator, the number of cells was counted. Based on these counts, the 50% inhibitory concentration ($IC_{50}$) of each test compound on the growth of L 1210 leukemia cells was calculated relative to the control test.

For measurement of $IC_{50}$ on the synthesis of nucleic acids, $5 \times 10^5$ L 1210 cells/ml were pre-cultured at 37° C. for 1–2 hours in RPMI 1640 medium containing 10% calf serum in a $CO_2$ incubator. One of the anthracyclinone glycosides listed in Table 4 was added and incubated for a further 15 minutes. Then 0.05 µCi/ml of $^{14}C$-uridine or $^{14}C$-thymidine was added and incubated for a further 60 minutes. At the end of incorporation of the radioactive compound, 10% trichloroacetic acid was poured into the cell suspension for termination of the reaction as well as forced precipitation. The acid-insoluble fraction was collected, rinsed three times with 5% trichloroacetic acid and then dissolved in formic acid for measurement of radioactivity. Based on the radioactivities of the test and control runs, $IC_{50}$ was calculated.

The results are summarized in Table 4, indicating the anthracyclinone glycosides of the present invention markedly inhibited the growth and the nucleic acid synthesis of L 1210 leukemia cells at a low concentration.

TABLE 4

| | $IC_{50}$ (µg/ml) | | |
|---|---|---|---|
| Compounds | Cell growth | DNA synthesis | RNA synthesis |
| Aclacinomycin A | 0.03 | 0.65 | 0.085 |
| Adriamycin | 0.018 | 1.25 | 0.49 |
| Daunomycin | 0.036 | 0.30 | 0.18 |
| 3''-O—acetyl AKN—RDC | 0.06 | 1.30 | 0.10 |
| 3''-O—acetyl DMN—RDC | <0.01 | 0.30 | 0.02 |
| DMN—RDC | <0.01 | 0.17 | 0.017 |
| DMN—RD | <0.01 | 0.28 | 0.04 |
| DMN—DmDC | 0.023 | 0.62 | 0.065 |
| DMN—DaDC | 0.09 | 1.15 | 0.165 |
| 14,3''-O—diacetyl AMN—RDC | <0.01 | 0.50 | 0.014 |
| 14-O—phenylacetyl-3''-O—acetyl AMN—RDC | 0.03 | 4.0 | 0.15 |
| 3''-O—acetyl AMN—RDC | <0.01 | 0.32 | 0.012 |
| AMN—RDC | <0.01 | 0.15 | 0.011 |
| 3''-O—acetyl CMN—RDC | <0.01 | 0.36 | 0.04 |
| CMN—RDC | <0.01 | 0.19 | 0.035 |

Experiments and examples that follow are to illustrate the anthracycline compounds produced by the present invention.

EXPERIMENT 1

4,6,3''-O-Triacetylaclacinomycin A

Aclacinomycin A (9.0 g) in a mixture of 40 ml acetic anhydride and 30 ml pyridine was stirred at 20° C. for 15 hours. After the reaction mixture was poured into 400 ml of ice water, the product was extracted with 200 ml of benzene. The organic layer was separated; rinsed with 5% monopotassium phosphate (200 ml ×3), 5% sodium bicarbonate (200 ml ×2) and water (200 ml ×2); dried over anhydrous sodium sulfate; and concentrated to dryness under reduced pressure. The residue was dissolved in a small volume of chloroform and then with a small volume of n-hexane. Removal of the solvents by evaporation yielded 10.2 g of a practically pure preparation (pale yellow powder) of 4,6,3''-O-triacetylaclacinomycin A. For further purification to the analytical grade, Sephadex LH-20 column chromatography was employed using acetone as eluent.

Melting point: 148°–151° C.
$[\alpha]_D^{24}$: +64.0° (c=0.05, CHCl$_3$)
UV: $\lambda_{max}^{CHCl_3}$ (E$_1$ $_{cm}$$^1$%): 261 nm (416), 344 nm (65)
IR: $\nu$cm$^{-1}$ (KBr): 1780, 1735, 1680
NMR (CDCl$_3$):
  $\delta$2.08 (3H, s, COCH$_3$)
  2.17 (6H, s, N(CH$_3$)$_2$)
  2.43 (3H, s, COCH$_3$)
  2.50 (3H, s, COCH$_3$)
  3.66 (3H, s, COOCH$_3$)
  4.9–5.4 (5H, m, C-1', C-1'', C-1''', C-3'', C-7 H)
  7.32–8.25 (4H, m, ArH)

EXPERIMENT 2

3'-O-Acetyl RDC

One gram of 4,6,3''-O-triacetylaclacinomycin A in 50 ml of methanol was hydrogenated at room temperature for 1 hour at atmospheric pressure in the presence of 1.0 g of 5% palladium-barium sulfate. After the solids were removed by filtration, the filtrate was concentrated to dryness at 30° C. under reduced pressure to give a yellowish brown oil. The oil was dissolved in 20 ml of chloroform and then extracted with 20 ml of 1% acetic acid. The aqueous layer was recovered; rinsed several times with small volumes of chloroform and adjusted to pH 8 with sodium bicarbonate. The product was extracted four times from the aqueous solution with 20 ml each of chloroform. The chloroform extracts were combined; dried over anhydrous sodium sulfate; and concentrated to dryness in vacuo to provide 479 mg (98% yield) of white powder of 3''-O-acetyl RDC.

Melting point: 64°–69° C.
$[\alpha]_D^{24}$: −237.6° (c=0.5, CHCl$_3$)
IR: $\nu$cm$^{-1}$ (KBr): 1730
NMR (CDCl$_3$):
  $\delta$1.1–1.3 (9H, m, 3CH$_3$)
  2.07 (3H, s, COCH$_3$)
  2.26 (6H, d, N(CH$_3$)$_2$)
  4.9–5.4 (4H, m, C-1', C-1'', C-1''' and C-3''H)

EXPERIMENT 3

14-O-Acetyl AMN . . . (1)

AMN (124 mg) was dissolved in 5 ml of acetic anhydride containing 0.5 g of boric acid and was kept stirred for one hour at 20° C. Then 0.15 ml of pyridine was added to the solution and the mixture was stirred for a further one hour. The reaction mixture was poured into 100 ml of ice water and subjected to chloroform extraction. After rinsing with water, the chloroform extract was dehydrated with anhydrous sodium sulfate and then concentrated to dryness under reduced pressure. The evaporation residue was purified by silica gel column chromatography using chloroform as developing solvent. Fractions containing the title compound only were combined and concentrated to dryness in vacuo to yield 91 mg of reddish orange powder of 14-O-acetyl AMN.

Melting point: 234°–237° C.
$[\alpha]_D^{24}$: +75.0° (c=0.02, CHCl$_3$)
UV-Vis: $\lambda_{max}^{CHCl_3}$ (E$_1$ $_{cm}$$^1$%):
  252 nm (546),
  287 nm (221),
  481 nm (263),
  496 nm (256),
  532 nm (132)
IR: $\nu$cm$^{-1}$ (KBr): 1730, 1610, 1575
NMR (CDCl$_3$+CD$_3$OD):
  $\delta$2.20 (3H, s, COCH$_3$)
  4.05 (3H, s, OCH$_3$)
  5.0–5.48 (3H, m, C-7H, COC$\underline{H}_2$OH)
  7.35–7.98 (3H, m, Ar H)

EXPERIMENT 4

14-O-Acetyl AMN . . . (2)

To a solution of 500 mg of daunomycin hydrochloride in a mixture of dry methanol (15 ml) and dry dioxane (30 ml), 1.77 ml of 10% (w/v) bromine in chloroform was added dropwise and the solution was agitated at 20° C. for 3 hours. The reaction mixture was diluted with 2.5 ml of water and then concentrated to a small volume in vacuo. The concentrate was mixed with a small amount of methanol and the solution was allowed to stand at room temperature for a while. Addition of water to the solution caused precipitation of reddish orange matters. The precipitates were collected by filtration, rinsed with water and desicated in vacuo to give 305 mg of 14-bromo DMN. Three hundred milligrams of 14-bromo DMN prepared as described above and 520 mg of anhydrous sodium acetate were suspended in 30 ml of acetone and heated under reflux for 1 hour. After insoluble matters were removed by filtration, the filtrate was concentrated to dryness under reduced pressure to provide a reddish brown residue. The residue was dissolved in 50 ml of chloroform and rinsed with 5% sodium bicarbonate (50 ml) and with water. The chloroform solution was dried over anhydrous sodium sulfate and then concentrated to dryness under reduced pressure. Silica gel column chromatography using chloroform as developing solvent produced 297 mg of reddish orange powder of 14-O-acetyl AMN from the evaporation residue. This preparation showed the same physicochemical properties as recorded in Experiment 3.

EXPERIMENT 5

14-O-Phenylacetyl AMN

According to the same experimental procedure as explained in Experiment 4, 14-bromo DMN was obtained. Subsequent treatment of 14-bromo DMN with anhydrous sodium phenylacetate in acetone gave orange powder of 14-O-phenylacetyl DMN.

Melting point: 175°–176° C.
$[\alpha]_D^{24}$: +75.6° (c=0.03, CHCl$_3$)
UV-Vis: $\lambda_{max}^{CHCl_3}$ (E$_1$ $_{cm}$$^1$%):
  252 nm (503),
  287 nm (190),
  480 nm (246),
  497 nm (237),
  533 nm (117)
IR: $\nu$cm$^{-1}$ (KBr): 1730, 1615, 1580
NMR (CDCl$_3$):
  $\delta$3.80 (2H, s, —CH$_2$Ar)
  4.98–5.46 (3H, m, C-7 H, COC$\underline{H}_2$OH)
  7.32 (6H, s+dd, C-3 H, Ar H)
  12.90 (1H, s, Ar OH)
  13.59 (1H, s, Ar OH)

EXAMPLE 1

3''-O-Acetyl AKN-RDC

Six hundreds milligrams of Molecular Sieves 4A were added into a reaction flask containing 311 mg of 3'-O-acetyl RDC, 0.26 ml of 2,4,6-collidine and 425 mg of tetra-n-butylammonium bromide in 3 ml of dry dichloromethane and the flask was cooled to −70° C. Under stirring, 0.13 ml of trifluoromethanesulfonic anhydride was added drop by drop to the flask with an injection syringe and the flask was kept stirred for 20 minutes, while the temperature of the solution was maintained at −70° C. After 140 mg of AKN in dry dichloromethane (6 ml) was added with an injection syringe, the reaction temperature was raised to room temperature at which the reaction was carried out for 5 hours under agitation. Insoluble matters were removed by filtration. The filtrate was diluted with 70 ml of benzene; rinsed twice with 70 ml each of 1% sodium bicarbonate, three times with 70 ml of 5% monopotassium phosphate and once with water; and dried over anhydrous sodium sulfate. The organic solution was concentrated to dryness under reduced pressure and the evaporation residue was subjected to silica gel column chromatography. Forty-two milligrams of unreacted AKN was recovered with an eluent of chloroform/methanol (100/1). 3″-O-Acetyl AKN-RDC (112 mg; yellow powder) was obtained by elution with an eluent of chloroform/methanol (200/3).

Melting point: 137°–140° C.
$[\alpha]_D^{24}$: −60.3° (c=0.05, CHCl$_3$)
UV-Vis: $\lambda_{max}^{CHCl_3}$ (E$_{1\ cm}$1% ):
  260 nm (311),
  292 nm (147),
  435 nm (166),
IR: $\nu cm^{-1}$ (KBr): 1735, 1675, 1625
FD-MS: m/z 853 (M+)
NMR (CDCl$_3$):
  δ2.06 (3H, s, COCH$_3$)
  2.17 (6H, s, N(CH$_3$)$_2$)
  3.67 (3H, s, COOCH$_3$)
  4.92–5.49 (5H, m, C-1′, C-1″, C-1‴, C-3″, C-7 H)
  7.20–7.82 (4H, m, Ar H)
  12.00 (1H, b, Ar OH)
  12.67 (1H, b, Ar OH)

EXAMPLE 2

3″-O-Acetyl DMN-RDC

To a solution containing 370 mg of 3′-O-acetyl RDC, 0.32 ml of 2,4,6-collidine and 515 mg of tetra-n-butylammonium bromide in 4 ml of dry dichloromethane, 800 mg of Molecular Sieves were added. Under cooling to −70° C. with agitation, 0.18 ml of trifluoromethanesulfonic anhydride was poured dropwise to the suspension with an injection syringe and allowed to react for 20 minutes. After 160 mg of DMN in 7 ml of dry dichloromethane was added with an injection syringe, the suspension was warmed to room temperature and was kept stirred for 5 hours. The Molecular Sieves were removed by filtration. The filtrate was diluted with 100 ml of benzene; and then rinsed with 1% sodium bicarbonate (100 ml ×2), 5% monopotassium phosphate (100 ml ×3) and water. The benzene solution was dried over anhydrous sodium sulfate and concentrated to dryness under reduced pressure. The evaporation residue was charged on a silica gel column and unreacted DMN (30 mg) was recovered by elution with chloroform. 3″-O-Acetyl DMN-RDC was eluted from the column with a solvent system of chloroform and methanol (100/1). The yield was 70.5 mg in orange powder.

Melting point: 147°–150° C.
$[\alpha]_D^{24}$: −60.4° (c=0.05, CHCl$_3$)
UV-Vis: $\lambda_{max}^{CHCl_3}$ (E$_{1\ cm}$1%):
  251 nm (282),
  287 nm (123),
  485 nm (134),
  499 nm (137),
  536 nm (78)
IR: $\nu cm^{-1}$ (KBr): 1730, 1625, 1585
FD-MS: m/z 840 (MH+)
NMR (CDCl$_3$):
  δ2.09 (3H, s, COCH$_3$)
  2.21 (6H, s, N(CH$_3$)$_2$)
  2.42 (3H, s, COCH$_3$)
  4.08 (3H, s, OCH$_3$)
  4.95–5.55 (5H, m, C-1′, C-1″, C-1‴, C-3″, C-7H)
  7.3–8.04 (3H, m, Ar H)
  13.22 (1H, s, Ar OH)
  13.88 (1H, s, Ar OH)

EXAMPLE 3

DMN-RDC and DMN-RD

A solution of 170 mg of 3″-O-acetyl DMN-RDC in a mixture of 12 ml of methanol and 2 ml of acetone was mixed with 10 ml of water and 1.4 ml of 1 N potassium carbonate. The mixture was stirred at 23° C. for 2.5 hours. After the pH of the reaction mixture was adjusted to 6 with 5% monopotassium phosphate, the methanol and the acetone were removed by evaporation under reduced pressure. The aqueous concentrate was extracted several times with chloroform. The chloroform extracts were combined, dried over anhydrous sodium sulfate and concentrated to dryness in vacuo to give 150 mg of an orange residue. By silica gel column chromatography using an eluent of chloroform and methanol (60/1), 36.7 mg of unreacted 3″-O-acetyl DMN-RDC (orange powder) and 40.6 mg of DMN-RDC (orange powder) were separated. DMN-RD (17.1 mg; orange powder) was eluted from the same column by increasing the relative amount of methanol in the eluent to 5/1.

DMN-RDC

Melting point: 145°–148° C.
UV-Vis: $\lambda_{max}^{CHCl_3}$ (E$_{1\ cm}$1%):
  250 nm (323),
  288 nm (117),
  485 nm (145),
  499 nm (149),
  536 nm (84)
IR: $\nu cm^{-1}$ (KBr): 1725, 1620, 1580
FD-MS: m/z 798 (MH+)
NMR (CDCl$_3$):
  δ2.19 (6H, s, N(CH$_3$)$_2$)
  2.40 (3H, s, COCH$_3$)
  4.06 (3H, s, OCH$_3$)
  5.01 (2H, m, C-1″, C-1‴ H)
  5.21 (1H, bs, C-7 H)
  5.50 (1H, bs, C-1′ H)
  7.2–8.0 (3H, m, Ar H)
  13.20 (1H, b, Ar OH)
  13.92 (1H, s, Ar OH)

DMN-RD

Melting point: 157°–161° C.
$[\alpha]_D^{20}$: +104° (c=0.02, CHCl$_3$)
UV-Vis: $\lambda_{max}^{CHCl_3}$ (E$_{1\ cm}$1%):
  250 nm (338),
  288 nm (126),
  485 nm (149),
  498 nm (153), 535 nm (86)
IR: $\nu cm^{-1}$ (KBr): 1715, 1620, 1580
FD-MS: m/z 686 (MH+)
NMR (CDCl$_3$):
  $\delta$2.21 (6H, s, N(CH$_3$)$_2$)
  2.40 (3H, s, COCH$_3$)
  4.05 (3H, s, OCH$_3$)
  5.00 (1H, bs, C-1″ H)
  5.22 (1H, bs, C-7 H)
  5.52 (1H, bs, C-1″ H)
  7.2–8.0 (3H, m, Ar H)
  13.17 (1H, bs, Ar OH)
  13.92 (1H, s, Ar OH)

EXAMPLE 4

DMN-DmDC and DMN-DaDC

A solution of 34 mg of DMN-RDC in 10 ml of chloroform was exposed to the sun light at 30° C. for 2.5 hours in a flat glass vessel. The chloroform solution was concentrated to dryness under reduced pressure. The evaporation residue was dissolved in a small volume of chloroform and subjected to preparative silica gel thin layer chromatography using an eluent of chloroform and methanol (10/1). DMN-DmDC (5.1 mg) and DMN-DaDC (2.7 mg) were recovered from the orange bands at Rf 0.27 and 0.23, respectively.

DMN-DmDC

Melting point: 149°–153° C.
UV-Vis: $\lambda_{max}^{CHCl_3}$ ($E_{1\ cm}^{1\%}$):
  250 nm (288),
  287 nm (105),
  483 nm (130),
  499 nm (134),
  535 nm (73)
IR: $\nu cm^{-1}$ (KBr): 1710, 1610, 1570
FD-MS: m/z 784 (MH+)
NMR (CDCl$_3$):
  $\delta$2.40 (6H, s, COCH$_3$, NHCH$_3$)
  4.04 (3H, s, OCH$_3$)
  5.00 (2H, m, C-1″, C-‴, H)
  5.23 (1H, bs, C-7 H)
  5.49 (1H, bs, C-1′ H)
  7.22–8.00 (3H, m, Ar H)

DMN-DaDC

Melting point: 161°–164° C.
UV-Vis: $\lambda_{max}^{CHCl_3}$ ($E_{1\ cm}^{1\%}$):
  250 nm (280),
  287 nm (108),
  483 nm (118),
  498 nm (121),
  535 nm (67)
IR: $\nu cm^{-1}$ (KBr): 1710, 1610, 1575
NMR (CDCl$_3$):
  $\delta$2.40 (3H, s, COCH$_3$)
  4.04 (3H, s, OCH$_3$)
  4.98 (2H, m, C-1″, C-1‴, H)
  5.24 (1H, bs, C-7 H)
  5.48 (1H, bs, C-1′ H)
  7.24–8.00 (3H, m, Ar H)

EXAMPLE 5

14,3″-O-Diacetyl AMN-RDC

Molecular Sieves 4A (1.2 g) were added to a solution of 600 mg of 3″-O-acetyl RDC and 0.52 ml of 2,4,6-collidine in 6 ml of dry dichloromethane. Under cooling to −70° C. with stirring, 0.3 ml of trifluoromethanesulfonic anhydride was dropped into the suspension with an injection syringe and allowed to react for 20 minutes at the said temperature. Using an injection syringe, first a solution of 835 mg of tetra-n-butylammonium bromide in 4 ml of dry dichloromethane and then a solution of 14-O-acetyl AMN in 10 ml of dry dichloromethane were added to the suspension. After warming to room temperature, the suspension was kept stirred for 2 hours. The filtrate was diluted with 200 ml of benzene and washed twice with 100 ml each of 1% sodium bicarbonate, three times with 100 ml each of 5% monopotassium phosphate and once with water. The benzene solution was dried with anhydrous sodium sulfate and subjected to evaporation under reduced pressure. The residue was dissolved in a small amount of chloroform and applied on top of a silica gel column. Unreacted 14-O-acetyl AMN (51 mg) was first eluted with a solvent mixure of chloroform and methanol (100/1). After the eluent was switched to a 20/1 mixture of chloroform and methanol, fractions containing 14,3″-O-diacetyl AMN-RDC only were collected and concentrated to dryness under reduced pressure. The final yield of the title compound (orange powder) was 86 mg.

Melting Point: 141°–144° C.
$[\alpha]_D^{24}$: −57.9° (c=0.027, CHCl$_3$)
UV-Vis: $\nu_{max}^{CHCl_3}$ ($E_{1\ cm}^{1\%}$):
  251 nm (270),
  286 nm (110),
  483 nm (105),
  498 nm (105),
  535 nm (58)
IR: $\nu cm^{-1}$ (KBr): 1735, 1620, 1580
NMR (CDCl$_3$):
  $\delta$2.07 (3H, s, COCH$_3$)
  2.18 (3H, s, COCH$_3$)
  2.21 (6H, s, N(CH$_3$)$_2$)
  4.05 (3H, s, OCH$_3$)
  4.85–5.52 (7H, m, C-1′, C-1″, C-1‴, C-3″, C-7 H, COCH$_2$OH)
  7.3–8.02 (3H, m, Ar H)
  13.22 (1H, bs, Ar OH)
  13.90 (1H, bs, Ar OH)

EXAMPLE 6

14-O-Phenylacetyl-3″-O-acetyl AMN-RDC

3′-O-Acetyl RDC (285 mg), 2,4,6-collidine (0.246 ml) and tetra-n-butylammonium bromide (400 mg) were dissolved in 3 ml of dry dichloromethane and 500 mg of Molecular Sieves 4 A were added. While the temperature of the suspension was maintained at −70° C. with agitation, 0.126 ml of trifluoromethanesulfonic anhydride was added drop by drop with an injection syringe and the suspension was allowed to react for 20 minutes at −70° C. 14-O-Phenylacetyl AMN (110 mg) in 4 ml of dry dichloromethane was poured with an injection syringe. After 5 hours of incubation at room temperature under stirring, the filtrate was subjected to the same purification procedure as described in Example 5 to give 44 mg of unreacted 14-O-phenylacetyl AMN and 49 mg of orange powder of 14-O-phenylacetyl-3′-O-acetyl AMN-RDC.

Melting point: 127°–131° C.
$[\alpha]_D^{24}$: −56.0° (c=0.05, CHCl$_3$)
UV-Vis: $\nu_{max}^{CHCl_3}$ ($E_{1\ cm}^{1\%}$):
  251 nm (252),
  286 nm (99), 483 nm (96),
498 nm (97),
535 nm (54)

IR: $\nu cm^{-1}$ (KBr): 1730, 1620, 1580
NMR (CDCl$_3$):
  $\delta$2.06 (3H, s, COCH$_3$)
  2.18 (6H, s, N(CH$_3$)$_2$)
  3.76 (2H, s, CH$_2$Ar)
  4.04 (3H, s, OCH$_3$)
  4.8–5.5 (7H, m, C-1', C-1", C-1''', C-3", C-7 H, COCH$_2$O)
  7.30 (6H, s+dd, C-3 H, Ar H)
  13.20 (1H, s, Ar OH)
  13.90 (1H, s, Ar OH)

EXAMPLE 7

3"-O-Acetyl AMN-RDC ... (1)

A solution of 70 mg of 14,3"-O-diacetyl AMN-RDC in a mixture of 3 ml of tetrahydrofuran and 7 ml of methanol was mixed with 1 ml of water and 1 N potassium carbonate and was then allowed to react at 20° C. for 10 minutes under stirring. The reaction mixture was poured into 10 ml of cold 1% monopotassium phosphate. After making alkaline with an aqueous solution of sodium bicarbonate, the solution was extracted three times with 20 ml each of chloroform. The chloroform extracts were combined, dried with anhydrous sodium sulfate and concentrated to dryness under reduced pressure. By silica gel column chromatography using a developing solvent system of chloroform and methanol (30/1), 35 mg of orange powder of 3"-O-acetyl AMN-RDC was obtained from the evaporation residue.

Melting point: 144°–147° C.
$[\alpha]_D^{24}$: −69.6° (c=0.05, CHCl$_3$)
UV-Vis: $\lambda_{max}^{CHCl_3}$ (E$_{1\,cm}$1%):
  251 nm (276),
  287 nm (118),
  483 nm (125),
  498 nm (126),
  535 nm (70)
IR: $\nu cm^{-1}$ (KBr): 1725, 1615, 1580
FD-MS: m/z 856 (MH+)
NMR (90 MHz, CDCl$_3$):
  $\delta$2.07 (3H, s, COCH$_3$)
  2.20 (6H, s, N(CH$_3$)$_2$)
  4.06 (3H, s, OCH$_3$)
  4.73 (2H, s, COCH$_2$O)
  5.05 (2H, m, C-1", C-1''' H)
  5.28 (1H, bs, C-7 H)
  5.51 (1H, bs, C-1' H)
  7.28–8.04 (3H, m, Ar H)
  13.22 (1H, bs, Ar OH)
  13.90 (1H, s, Ar OH)

EXAMPLE 8

3"-O-Acetyl AMN-RDC ... (2)

To a solution of 30 mg of 14-O-phenylacetyl-3"-O-acetylAMN-RDC in a mixture of 2 ml of tetrahydrofuran and 4 ml of acetone, 1 ml of water and 0.24 ml of 1 N potassium carbonate were added and kept stirred at room temperature for 5 hours. By the same purification procedure as detailed in Example 7, 10.2 mg of 3"-O-acetyl AMN-RDC was obtained.

EXAMPLE 9

AMN-RDC

14-O-Phenylacetyl-3"-O-acetyl AMN-RDC (34 mg) was dissolved in a mixture of 1 ml of acetone and 3 ml of methanol and was then mixed with 0.17 ml of 1 N potassium carbonate and 3 ml of water. After agitation at 22° C. for one and a half hour, the reaction mixture was made acidic by addition of 1% monopotassium phosphate. The acidic solution was again made alkaline with saturated sodium bicarbonate solution and extracted with chloroform. Evaporation of the chloroform from the combined chloroform extracts under reduced pressure provided a residue which was subjected to preparative silica gel thin layer chromatography using a solvent of chloroform and methanol (10/1). An orange powder of AMN-RDC (7.6 mg) was obtained from the area of silica gel corresponding to Rf 0.44.

Melting point: 154°–157° C.
UV-Vis: $\lambda_{max}^{CHCl_3}$: 251 nm, 287 nm, 483 nm, 498 nm, 535 nm
IR: $\nu cm^{-1}$ (KBr): 1720, 1615, 1580
NMR (CDCl$_3$):
  $\delta$2.18 (6H, s, N(CH$_3$)$_2$)
  4.08 (3H, s, OCH$_3$)
  4.72 (2H, s, COCH$_2$OH)
  5.00 (2H, m, C-1", C-1''' H)
  5.27 (1H, bs, C-7 H)
  5.51 (1H, bs, C-1' H)
  7.25–8.05 (3H, m, Ar H)
  13.30 (1H bs, Ar OH)
  13.97 (1H, s, Ar OH)

EXAMPLE 10

3"-O-Acetyl CMN-RDC

CMN (110 mg), tetra-n-butylammonium bromide (750 mg) and Molecular Sieves (4.0 g) were suspended in 40 ml of dichloromethane and cooled to 0° C. To this suspension was added with an injection syringe a reaction mixture resulting from treatment of 400 mg of 3'-O-acetyl RDC with 74 μl of methanesulfonyl chloride at −10° C. in the presence of 154 μl of 2,4,6-collidine. After reaction for 6 hours at about 22° C., the same reaction mixture of methanesulfonylated 3'-O-acetyl RDC (400 mg) was supplemented and was kept stirred overnight at room temperature. The filtrate was concentrated to dryness under reduced pressure. The evaporation residue was dissolved in 100 ml of benzene; rinsed with 5% monopotassium phosphate (100 ml×3), 5% sodium carbonate (100 ml) and water; and dried over anhydrous sodium sulfate. Benzene was removed by evaporation in vacuo. The residue was dissolved in a small volume of chloroform and filtered for separation of insoluble matters (insoluble matters consisting of 64 mg of unreacted CMN). The filtrate was applied on preparative silica gel thin layer plates and developed in a solvent system of chloroform and methanol (10/1). The zones of silica gel at Rf 0.47 yielded 36 mg of orange powder of 3"-O-acetyl CMN-RDC.

Melting point: 140°–143° C.
$[\alpha]_D^{22}$: −59.5° (C=0.05, CHCl$_3$)
UV-Vis: $\lambda_{max}^{CHCl_3}$ (E$_{1\,cm}$1%):
  254 nm (349),
  292 nm (113),
  472 nm (153),
  495 nm (199), 517 nm (141),
531 nm (137)
IR: $\nu cm^{-1}$ (KBr): 1725, 1600
NMR (CDCl$_3$):
  $\delta$2.10 (3H, s, COCH$_3$)
  2.24 (6H, s, N(CH$_3$)$_2$)
  2.42 (3H, s, COCH$_3$)
  5.01 (1H, t, C-1''' H)
  5.05 (1H, bs, C-1'' H)
  5.22 (2H, bs+m, C-7, C-3'' H)
  5.49 (1H, bs, C-1' H)
  7.17-7.88 (3H, m, Ar H)
  11.00 (1H, b, Ar OH)
  11.78 (1H, b, Ar OH)
  12.36 (1H, bs, Ar OH)

EXAMPLE 11
CMN-RDC

3''-O-Acetyl CMN-RDC (20 mg) in a mixture of 1 ml of acetone and 4 ml of methanol was mixed with 1.22 ml of 0.1 N NaOH and 4 ml of water and agitated at 24° C. for 2 hours. After terminating the reaction by weak acidification with a monopotassium phosphate solution, the reaction mixture was again made alkaline with a sodium bicarbonate solution and extracted with 20 ml of chloroform. The chloroform extract was washed several times with small volumes of water and concentrated to dryness under reduced pressure. The evaporation residue was subjected to preparative silica gel thin layer chromatography with a solvent system of chloroform and methanol (10/1). The silica gel collected at Rf 0.41 yielded 7.1 mg of CMN-RDC (orange powder).

Melting point: 151°-154° C.
UV-Vis: $\lambda_{max}^{CHCl_3}$: 255 nm, 292 nm, 470 nm, 496 nm, 517 nm, 532 nm
IR: $\nu cm^{-1}$ (KBr): 1730, 1600
NMR (CDCl$_3$):
  $\delta$2.23 (6H, s, N(CH$_3$)$_2$)
  2.41 (3H, s, COCH$_3$)
  4.92-5.53 (4H, m, C-1', C-1'', C-1''', C-7 H)
  7.18-7.90 (3H, m, Ar H)

What is claimed is:

1. Novel anthracyclinone glycosides represented by the chemical formula:

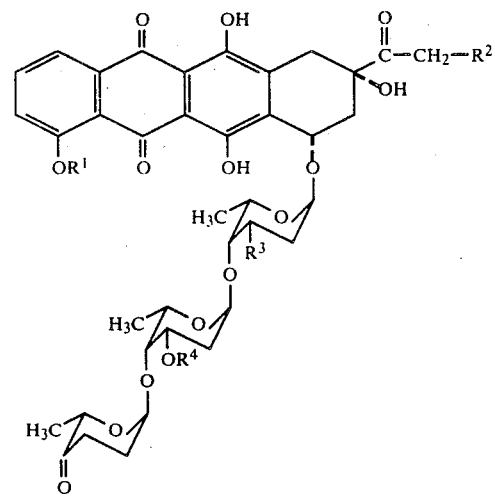

wherein
R$^1$ is hydrogen or methyl;
R$^2$ is hydrogen, hydroxyl or —OCOX (wherein X is lower alkyl or aralkyl);
R$^3$ is amino, monomethylamino or dimethylamino; and
R$^4$ is hydrogen or acetyl;

and their acid addition salts.

2. The anthracyclinone glycoside compounds represented by chemical formula (I) and their acid addition salts defined in claim 1, in which R$^1$ is methyl; R$^2$ is hydrogen, hydroxyl or —OCOX (wherein X is lower alkyl or aralkyl); R$^3$ is amino, monomethylamino or dimethylamino, and R$^4$ is hydrogen or acetyl.

3. The anthracyclinone glycoside compounds represented by chemical formula (I) and their acid addition salts defined in claim 1, in which R$^1$ is hydrogen; R$^2$ is hydrogen; R$^3$ is amino, monomethylamino or dimethylamino, and R$^4$ is hydrogen or acetyl.

4. The anthracyclinone glycoside compound and its acid addition salts defined in claim 2, which is represented by the chemical formula:

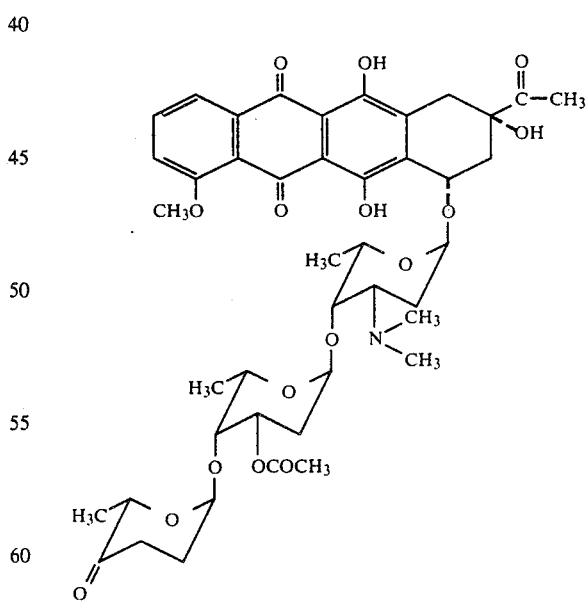

5. The anthracyclinone glycoside compound and its acid addition salts defined in claim 2, which is represented by the chemical formula:

6. The anthracyclinone glycoside compound and its acid addition salts defined in claim 3, which is represented by the chemical formula:
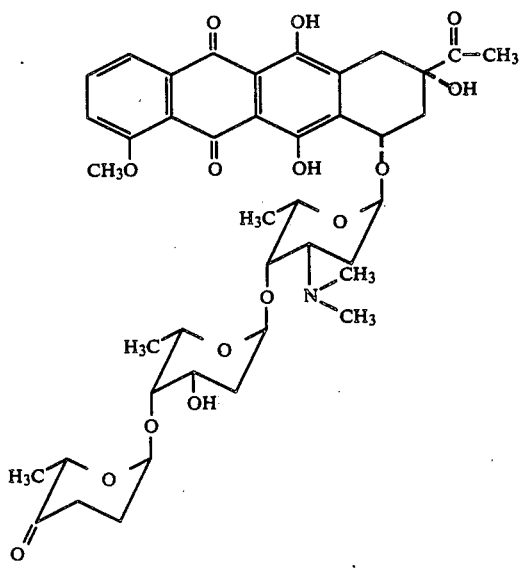
7. The anthracyclinone glycoside compound and its acid addition salts defined in claim 3, which is represented by the chemical formula:
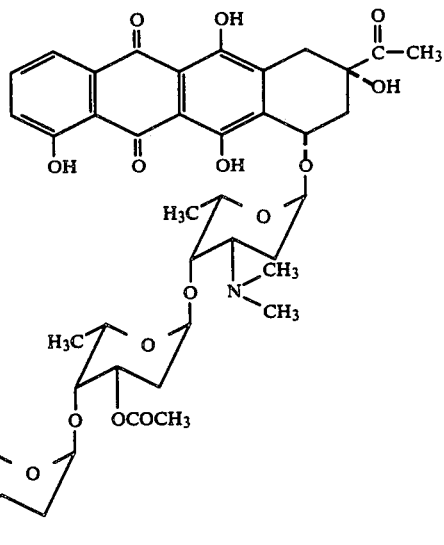
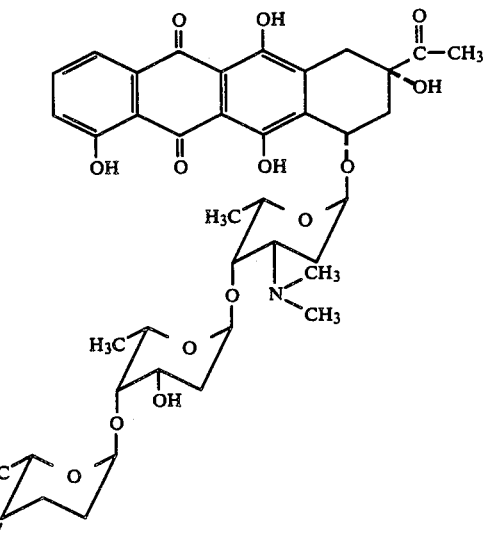
* * * * *